US012766035B2

(12) United States Patent
Govari et al.

(10) Patent No.: US 12,766,035 B2
(45) **Date of Patent: *Oct. 20, 2026**

(54) SURGICAL SYSTEM PRIMING WITH PRESSURE CALIBRATION

(71) Applicant: JOHNSON & JOHNSON SURGICAL VISION, INC., Irvine, CA (US)

(72) Inventors: Assaf Govari, Haifa (IL); Andres Claudio Altmann, Haifa (IL); Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 394 days.

This patent is subject to a terminal disclaimer.

(21) Appl. No.: 18/532,451

(22) Filed: Dec. 7, 2023

(65) Prior Publication Data

US 2025/0186256 A1 Jun. 12, 2025

(51) Int. Cl.

*A61F 9/00* (2006.01)
*A61F 9/007* (2006.01)
(Continued)

(52) U.S. Cl.

CPC ....... *A61F 9/00781* (2013.01); *A61M 3/0216* (2014.02); *A61M 3/0283* (2013.01); (Continued)

(58) Field of Classification Search

CPC .. A61F 9/00763; A61F 9/007; A61F 9/00736; A61F 9/00745; A61M 1/774; A61M 1/77; A61M 1/772

See application file for complete search history.

(56) References Cited

U.S. PATENT DOCUMENTS 7,326,183 B2 2/2008 Nazarifar et al.
7,509,831 B2 3/2009 Khashayar
(Continued)

FOREIGN PATENT DOCUMENTS

EP 1 550 423 B1 12/2008
EP 1 896 826 B1 9/2013
(Continued)

OTHER PUBLICATIONS

Han et al., "Comparison of Vacuum Rise Time, Vacuum Limit Accuracy, and Occlusion Break Surge of 3 New Phacoemulsification Systems", Journal Cataract and Refractive Surgery, vol. 35, No. 8, pp. 1424-1429, Aug. 1, 2009.
(Continued)

*Primary Examiner* — Courtney Fredrickson

(57) ABSTRACT

A phacoemulsification system and a corresponding method are described. The system having a handpiece having a needle and a sleeve at a distal end to emulsify a lens of an eye; an irrigation module configured to supply irrigation fluid into the eye; an aspiration module configured for aspiring eye fluid; a priming cover for fitting over the distal end of the handpiece during a priming process; external pressure sensors coupled with the priming cover; one or more sensors for monitoring at least one of an irrigation pressure and an aspiration pressure; and a processor configured to operate in a priming process. The priming process includes operating the irrigation module to fill the irrigation channel with fluid and remove air bubbles. The one or more processors are configured for obtaining calibration pressure data from the external pressure sensors and for calibrating the sensors of the system.

7 Claims, 4 Drawing Sheets

(51) Int. Cl.
*A61M 3/02* (2006.01)
*A61B 17/00* (2006.01)
*A61B 90/00* (2016.01)

(52) U.S. Cl.
CPC ............... *A61B 2017/00402* (2013.01); *A61B 2090/064* (2016.02); *A61B 2217/005* (2013.01); *A61B 2217/007* (2013.01); *A61M 2205/3344* (2013.01); *A61M 2205/3348* (2013.01); *A61M 2205/702* (2013.01)

(56) References Cited

U.S. PATENT DOCUMENTS

| | | | | |
|---|---|---|---|---|
| 7,644,603 | B2 | 1/2010 | Gordon et al. | |
| 7,648,465 | B2 | 1/2010 | Gordon | |
| 10,376,328 | B2 | 8/2019 | Charles et al. | |
| 10,702,415 | B2 | 7/2020 | Charles | |
| 11,317,983 | B2 | 5/2022 | Charles et al. | |
| 11,806,465 | B2 | 11/2023 | Govari et al. | |
| 2008/0006096 | A1 | 1/2008 | Gordon et al. | |
| 2008/0110236 | A1 | 5/2008 | Hajishah et al. | |
| 2008/0289398 | A1* | 11/2008 | Khashayar | A61M 5/14526 73/37 |
| 2014/0315174 | A1 | 10/2014 | Sassani et al. | |
| 2018/0055592 | A1 | 3/2018 | Charles et al. | |
| 2021/0386928 | A1 | 12/2021 | Mehta et al. | |
| 2022/0008251 | A1* | 1/2022 | Govari | A61F 9/00736 |
| 2022/0211931 | A1 | 7/2022 | Kuntz et al. | |
| 2022/0339034 | A1 | 10/2022 | Govari et al. | |
| 2023/0255821 | A1 | 8/2023 | Gliner et al. | |
| 2023/0347046 | A1 | 11/2023 | Blanco et al. | |
| 2023/0364320 | A1 | 11/2023 | Gliner et al. | |
| 2025/0221852 | A1 | 7/2025 | Govari et al. | |

FOREIGN PATENT DOCUMENTS

| | | | |
|---|---|---|---|
| WO | 2022224076 | A1 | 10/2022 |
| WO | 2023152585 | A1 | 8/2023 |
| WO | 2023170498 | A1 | 9/2023 |

OTHER PUBLICATIONS

Nicoli et al., "Experimental Anterior Chamber 2 Maintenance in Active Versus Passive Phacoemulsification Fluidics Systems", Journal Cataract and Refractive Surgery, vol. 42, pp. 157-162, 2016.

* cited by examiner

SURGICAL SYSTEM PRIMING WITH PRESSURE CALIBRATION

TECHNOLOGICAL FIELD

The present disclosure relates to priming of surgical system, and more particularly relates to priming of phacoemulsification system while calibrating pressure of fluid in the system.

BACKGROUND #

Phacoemulsification is a surgical procedure used to treat cataracts, which is associated with clouding of the eye's lens and can cause blurred vision, difficulty seeing at night, and sensitivity to light. during the procedure, a surgeon makes a small incision in the patient's cornea and inserts a probe to emit ultrasonic waves breaking the cataract tissue to small pieces. The pieces of the tissue can be suctioned out of the eye, where an artificial lens can be placed.

Typically, prior to surgical operation, the phacoemulsification undergoes priming and/or tuning to prepare the system for required operation. Priming of the system generally involves filling the phacoemulsification system tubing with irrigation fluid (typically balanced salt solution) and creating vacuum in the system.

The priming process is important for ensuring safety and effectiveness of the surgical operation, it helps prevent air bubbles from entering the eye and reduces surgical risks. Generally, the intraocular pressure (IOP) needs to be closely monitored during the phacoemulsification procedure to avoid damage to the patient's eye as a result of vacuum surge or fluid accumulation. To this end phacoemulsification systems typically include sensors monitoring irrigation and vacuum pressures and adjust the pressures to maintain IOP.

General Description

Correspondence between the actual IOP and the readings from the irrigation pressure provided by sensors of the phacoemulsification systems may depend on various factors including distance of the sensors from the tip of the needle, mechanical structure of the handle as well as ambient conditions. This limits the accuracy in determining IOP during the procedure.

As indicated above, priming process generally includes operation of a phacoemulsification system for providing irrigation fluid within respective channels and removing air bubbles from the irrigation channel. During the priming process, the system may also operate to tune one or more sensors thereof, verifying accurate pressure and flow reading during operation. The Present disclosure provides a method and system for priming phacoemulsification systems to enhance accuracy and reproducibility in IOP pressure estimation during the procedure.

More specifically, the present disclosure provides a phacoemulsification system, and a method for use in priming of a phacoemulsification system, utilizing one or more external pressure sensors coupled with or connected to an operation (distal) end of a handpiece of the phacoemulsification system. The one or more external pressure sensors are used for determining fluid pressure during priming of the system, enabling calibration of one or more internal pressure sensors of the system, and allowing direct and accurate control of irrigation and/or aspiration pressure during surgical operation. Accordingly, when the phacoemulsification system operates in a priming mode, typically prior to performing a medical procedure, the system utilizes the one or more external pressure sensors to obtain calibration pressure data and to calibrate pressure output data of the one or more internal sensors. The one or more internal sensors are used for monitoring irrigation and/or aspiration pressures during surgical operation.

BRIEF DESCRIPTION OF THE DRAWINGS

In order to better understand the subject matter that is disclosed herein and to exemplify how it may be carried out in practice, examples will now be described, by way of non-limiting example only, with reference to the accompanying drawings, in which.

DETAILED DESCRIPTION OF EXAMPLES

Figure 1:
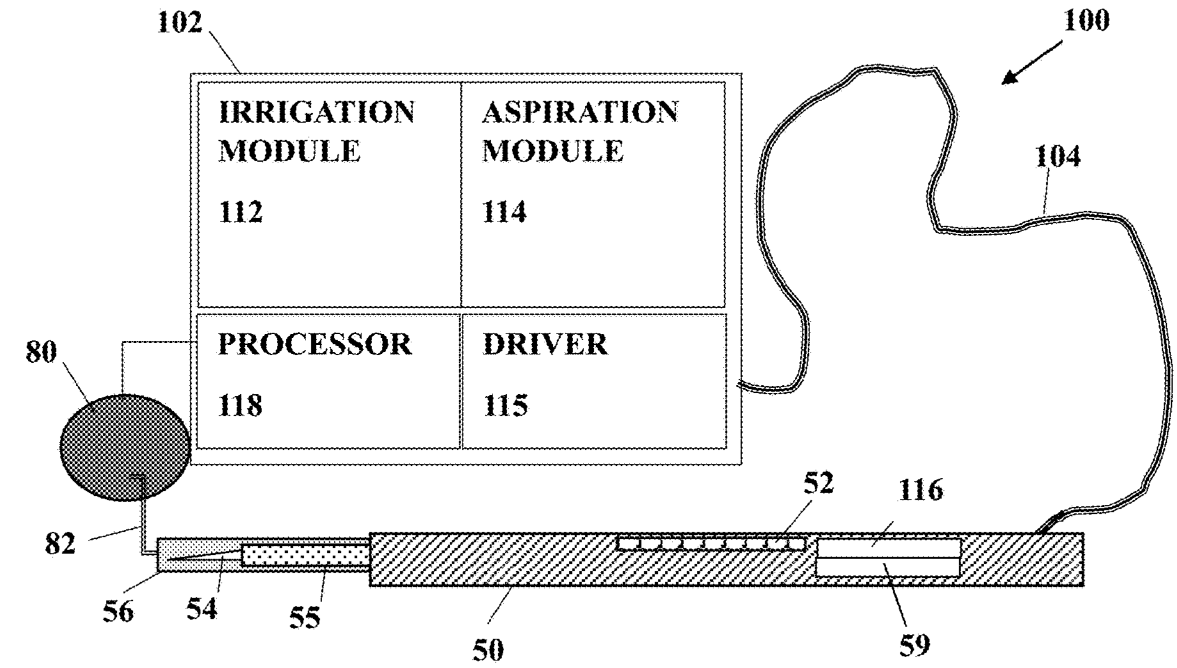
FIG. 1 schematically illustrates a phacoemulsification system utilizing one or more external pressure sensors according to some examples of the present disclosure.

As indicated above, the present disclosure provides a method and a phacoemulsification system utilizing one or more external sensors operable for calibration pressure sensor during pre-use priming process. Reference is made to FIG. 1 schematically illustrating a phacoemulsification system 100 according to some examples of the present disclosure. The system 100 includes a handpiece 50 coupled with unit 102 via connection line 104 configured to provide irrigation, aspiration, and additional functionalities, e.g., power, to the handpiece 50.

Handpiece 50 may include at least one vibrating element 52, e.g., piezoelectric crystal and corresponding circuitry, and a needle 54 and sleeve 55 located at a distal end of the handpiece 50. Vibrating element 52 is operable for vibrating at a selected frequency to emulsify a lens of a patient's eye during a surgical procedure. Additionally, needle 54 and sleeve 55 may provide a portion of irrigation and aspiration channels to transmit irrigation fluid and to apply aspiration vacuum at the operation site as described in more details below. Handpiece 50 may include one or more sensors 116, internal channels associated with aspiration channel and irrigation channel. Further, handpiece 50 may also include anti-vacuum surge (AVS) module 59 configured to block aspiration flow in response to detection. AVS 59 may be coupled with or connected to sensors 116 for receiving data on pressure and/or flow rate in the irrigation and/or aspiration channels and operate to block aspiration pressure from reaching the patient's eye in response to detecting conditions indicating possible vacuum surge.

In this connection it should be noted that the one or more sensors 116 may be located within the handpiece 50, within the main unit 102, and/or incorporated within the AVS module 59.

The needle 54 and sleeve 55 located at distal end of the handpiece 50 provide irrigation and aspiration to the eye, as well as transmit vibrations to emulsify lens material. Typically, in some examples, irrigation fluid may flow into eye volume through a region between outer wall of the needle 54 and inner wall of the sleeve 55. While in some configurations, aspiration channel may flow through the needle 54.

Generally, handpiece 50 may be electronically coupled with the one or more processors 118 (or PMC as described below) and may provide an interface enabling a physician, scrub nurse, or other operator, to operate the phacoemulsification system and control its operational parameters. The handpiece may be coupled with an operation interface in the form of buttons, dials, touchscreen section, foot pedal etc., enabling a physician to provide operation instructions to the processor 118. More specifically, an operator, being a surgeon, nurse or technician may control and/or program selected operations using the user interface and one or more input methods such as a button, pedal, etc. Certain exemplary configurations of the handpiece are described in U.S. Pat. No. 11,806,465 assigned to the assignee of the present application and incorporated herein by references.

Unit 102 may include irrigation module 112, aspiration module 114, driver module 115 and processor 118. As indicated above, unit 102 may in some configurations include one or more sensors 116. The processor 118 is typically associated with a memory and input/output interface, providing a processor and memory circuitry (PMC). The processor, or PMC 118 is operatively coupled with the input/output interface and configured to provide processing necessary for operating system 100 as further described. The processor 118 can be configured to execute several functional modules in accordance with computer readable instructions stored in the memory and/or implemented via one or more computer readable media. Processor 118 may operate irrigation module 112, aspiration module 114, and driver 115 in accordance with one or more operation schemes determined by an operator (e.g., physician or nurse). As indicated above, the operator may determine an operation scheme and parameters via the user interface including e.g., one or more buttons/pedals as described above.

Phacoemulsification system 100 is configured and operable for performing one or more medical operations, such as cataract operation. The system is further configured for operating in a pre-operation priming and/or tuning mode. In the pre-operation priming and/or tuning mode, phacoemulsification system 100 may operate to prepare the system for operation, typically by flowing fluid through the irrigation and/or aspiration channels and ensuring selected pressure conditions required for suitable operation of the system. To this end, the phacoemulsification system 100 further includes a priming cover (also known as a test chamber) 56 configured to fit on and provide cover to the distal end of the handpiece 50, including covering the needle and sleeve 54 thereof. The priming cover 56 is connected or connectable with one or more external sensors 80, e.g., pressure sensors, via channel 82. The one or more external sensors 80 is configured to provide sensing data indicative of pressure (e.g., fluid pressure) through the priming cover 56 and needle and sleeve 54. The one or more external sensors 80 is connectable to unit 102 to provide output sensing data to the one or more processors 118 thereof. In some examples of the present disclosure, the one or more processors 118 utilize pressure data collected from the one or more external sensors 80 to calibrate the one or more sensors 116 of the system.

Generally, a phacoemulsification system may be used in a cataract procedure. During the procedure, distal end of the handpiece may be directed into a patient's eye through a small incision in the sclera or cornea. The needle of the handpiece may vibrate using the piezoelectric vibrating element 52 to emulsify the lens of the eye. The system is further operated to provide irrigation fluid into the eye, and to aspirate the irrigation fluid together with other fluids in the eye and the emulsified lens, forming together eye fluids, to remove the fluids from the eye. Pressure variation within the patient's eye is preferably minimized to avoid collapse of the cornea and maintain eye structure to avoid surgical complications.

According to some examples of the present disclosure, phacoemulsification system 100 may carry pre-stored computer readable instructions indicative of a priming mode operation. The pre-stored instructions include instructions that when executed by the one or more processors 118, cause the processor to operate the irrigation module 112 and aspiration module 114 for preparing the respective irrigation and aspiration lines extending between unit 102 and handpiece 50 to allow fluid flow between the distal end of the handpiece 50 and the respective modules 112 and 114. The pre-stored instruction also includes instructions to obtain calibration pressure data from the one or more external sensors 80, indicative of pressure detected at the distal end of the handpiece 50, and use the calibration pressure data to calibrate one or more sensors 116.

Connection line 104 may be of a selected length providing maneuverability in position of handpiece 50 to allow a physician to perform the required medical operation. Connection line 104 may include tubing for irrigation and aspiration and additional wiring for communication between the handpiece 50 and unit 102. In some examples, as mentioned above, one or more sensors 116 may be placed within unit 102, and configured for collecting sensing data along the irrigation and/or aspiration channels. In such configurations, length and path of the connection line 104, may result in variation between the pressure measured by sensors 116 and actual pressure at the distal end of handpiece 50.

Additionally, as exemplified in FIG. 1, one or more sensors 116 may be placed within the handpiece, or at a selected location along connection line 104. This location of the sensor(s) 116 may simplify the structure of the system. However, distance between the one or more sensors 116 and distal end, or tip of the needle 54, of handpiece 50 may still cause variation between measured pressure and actual pressure at the distal end of the handpiece. Additionally, in some configurations, tubing compliance issues, associated with tubing between the distal end of handpiece 50 and the one or more sensors 116 may also affect pressure measurements.

More specifically, according to some examples, prior to performing a medical operation, phacoemulsification system 100 is operable in priming and/or tuning mode. While operating in priming and/or tuning mode, the system 100 operates the irrigation module 112, typically including at least one pump and coupled with a fluid reservoir (not specifically shown), for pushing fluid through irrigation channel toward the needle 54 and sleeve 55 at the distal end of the handpiece. This is performed to ensure that the irrigation channel is filled with fluid and any air bubbles are removed. Additionally, the system 100 operates the aspiration module 114, typically including at least one pump configured to apply vacuum conditions though the aspiration channel, via needle 54 to pull the fluid introduced by the irrigation module through the aspiration module and remove any air bubbles in the system. Additionally, according to some examples of the present disclosure, at least one processor 118 operates to obtain pressure data from one or more internal sensors 116 and from one or more external sensors 80. The at least one processor further operates to calibrate pressure readout of the one or more pressure sensors 116 in accordance with calibration pressure data obtained from the one or more external sensors 80. The at least one processor 118 may operate to determine a relation, or a function defining a relation between pressure output of the one or more sensors 116 and the pressure data obtained from one or more external sensors 80. For example, in some situations, pressure detected by one or more sensors 116 may be lower (or higher) than pressure detected by one or more external sensors 80 by a fixed pressure difference. In such cases, the determined relation may be determined as $P_{116}=P_{80}+\Delta P$, where $P_{116}$ is pressure data detected by one or more pressure sensors 116, $P_{80}$ is pressure data detected by one or more external sensors 80, and $\Delta P$ is the detected pressure difference. In some other situations, pressure detected by one or more sensors 116 may be lower (or higher) than pressure detected by one or more external sensors 80 by certain ratio. In such cases, the determine relation may be of the form $P_{116}=P_{80}*R$, where $P_{116}$ is pressure data detected by one or more pressure sensors 116, $P_{80}$ is pressure data detected by one or more external sensors 80, and R is the determine ratio, being smaller or greater than unity. In some situations, the determined relation may be linear, in the form $P_{116}=P_{80}*R+\Delta P$. In some other situations, the determined relation may include a quadratic factor or other factors as determined by the one or more processors 118 during calibration.

After determining the relation between the pressure data measured by the one or more external sensors 80 and one or more sensors 116, the one or more processors 118 may operate to determine a calibration factor, or calibration function, enabling conversion of pressure data determined by one or more sensors 116 and the pressure that is determined by one or more external sensors 80. The at least one processor 118 may operate to store the calibration factor in a respective memory unit, together with instructions on conversion of pressure output from one or more sensors 116 during operation in accordance with the calibration factor. Thus, system 100, or the at least one processor 118 thereof may utilize the calibration factor to adjust output data indicative of fluid pressure obtained from the one or more sensors 116 system during operation to provide data on pressure that is adjusted to pressure at the distal end of the handpiece.

The one or more external sensors 80 may be fully external to phacoemulsification system 100, or be a part of the system. In this connection, the one or more externals sensors 80 may be external in the sense of measuring pressure at an external location, i.e., measure pressure at distal end of the handpiece 50 via priming cover 56. The one or more external sensors 80 may include any type of sensor capable of detecting pressure variation, including for example, capacitive sensors, strain gauge sensor, piezoelectric sensor, bourdon type sensor, manometer sensor, etc.

Figure 2:
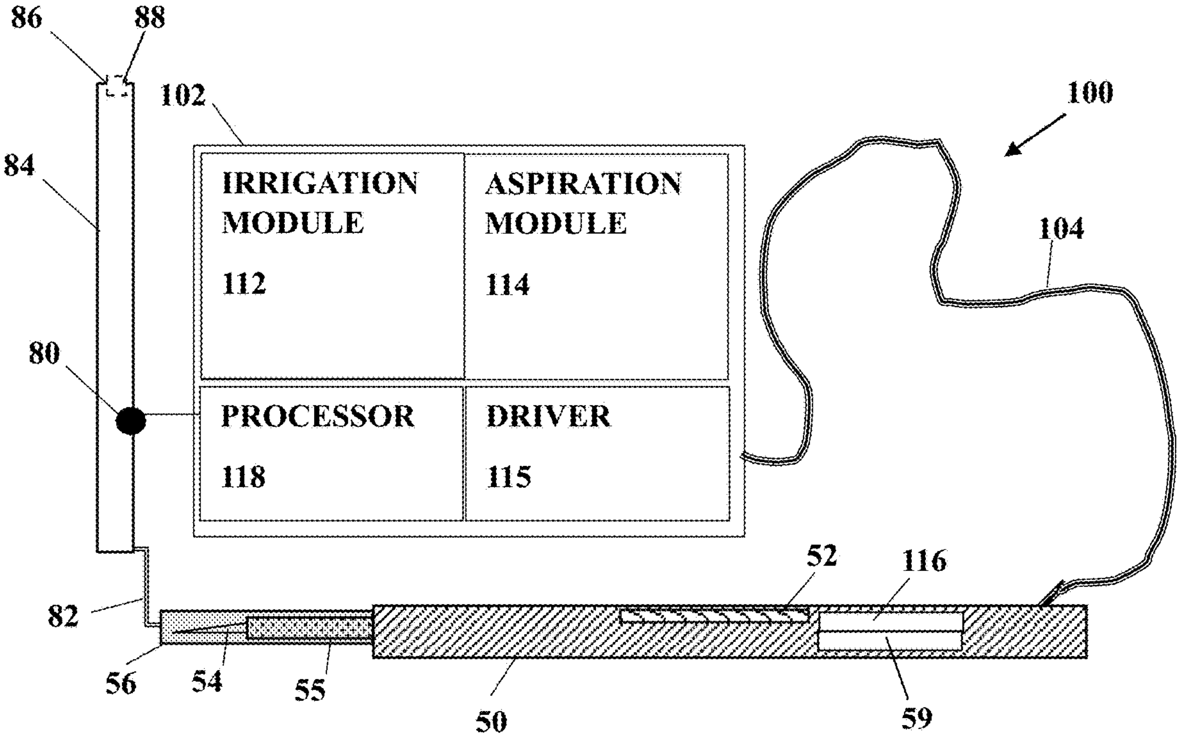
FIG. 2 schematically illustrates another phacoemulsification system utilizing one or more external pressure sensors and a water column according to some examples of the present disclosure.

In this connection, reference is made to FIG. 2 illustrating schematically a phacoemulsification system 100 according to some examples of the present disclosure. The configuration of FIG. 2 is generally similar to that of FIG. 1, except that the one or more external sensors 80 is coupled with a water column 84. Water column 84 provides a relatively simple and reliable pressure measurement. Water column 84 may be associated with one or more sensors 80 configured for determining height of the water column 80 and using height data to determine fluid pressure as measured at the priming cover 56. Additionally, or alternatively, one or more sensors 80 may include a capacitive sensor, or any other type of pressure sensor, associated with a diaphragm being in fluid communication with fluid in the water column 84.

As indicated above, the one or more external sensors 80, and/or water column 84 when used, may be physically external to the phacoemulsification, coupled with the frame of unit 102, or form an integral part of phacoemulsification system 100. In some examples, where the one or more external sensors 80 and/or water column 84, are integral part of the system, the one or more sensors are external in the meaning that the sensors 80 are connected to determine pressure data at the distal end of handpiece 50, through priming cover 56.

Figure 3A:
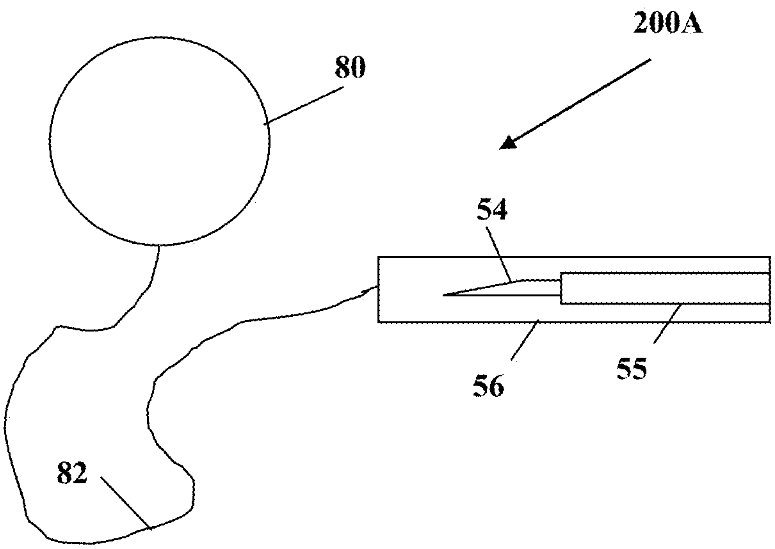
FIGS. 3A and 3B exemplify an external sensor kit according to some examples of the present disclosure, FIG. 3A exemplifies a kit including a priming cover and a sensor and FIG. 3B exemplifies a kit including a priming cover and a water column.
Figure 3B:
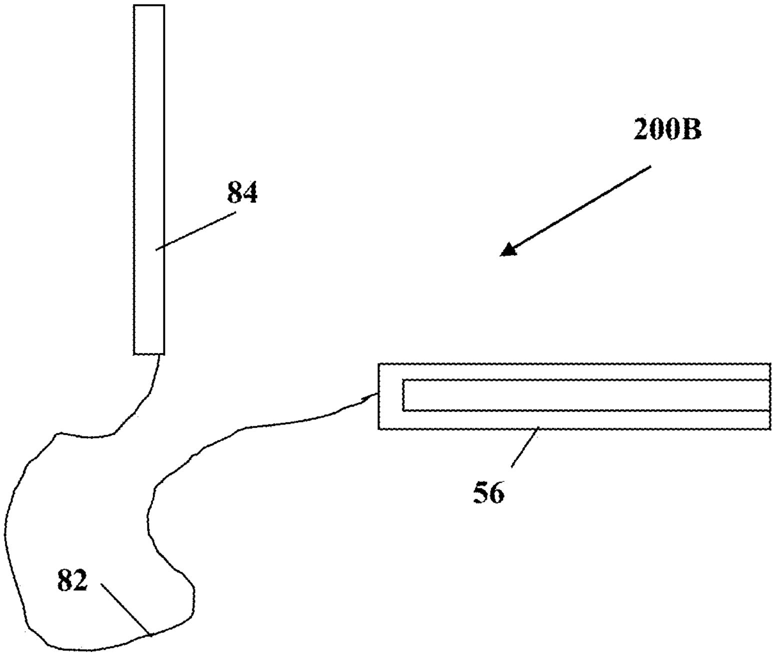

Additionally, priming cover 56, together with at least one or more channels (tubes) 82, connecting the priming cover to the one or more external sensors 80 and/or to water column 84, may be sterilized prior to use. Accordingly, in some examples, a priming kit, including at least a priming cover 56 connected via channel 82 to one or more externals sensors 80 may be used separately from phacoemulsification system 100. This is exemplified in FIGS. 3A and 3B, illustrating two examples of external sensor kits 200A and 200B according to some examples of the present disclosure. External sensor kit 200A includes at least a priming cover 56 coupled with one or more pressure sensors 80 via a channel 82. External sensor kit 200B includes at least a priming cover 50 connected with or connectable with water column 84 via channel 82, where water column 84 is connectable to one or more sensors. The kits 200A or 200B may be connectable to a separate sensor 80 or include one or more sensors 80 in accordance with technical design or include the sensor as part of the kit. External sensor kits 200A or 200B may be disposable, and/or suitable for re-sterilization between uses.

In some examples, the water column 84 may be sufficiently tall to enable pressure measurements with a working range of 700 mmHg, to thereby enable pressure measurement within a typical working pressure range of the phacoemulsification system. In some other examples, the height of the water column may be reduced, to provide a relatively compact system. Accordingly, for the case of a reduced height water column 84, the present technique may utilize one or more approximation techniques to determine pressure variations, such as assuming linearity in pressure variation and water level and extrapolate actual pressure from the water column level.

Additionally, in some examples, the water column 84 may include one or more apertures 86 associated with one or more flow meters 88 located at top end of the water column 84. In these examples, one or more external sensors 80 may be associated with flow meter 88 located at the one or more apertures of the water column 84 to provide data indicative of pressure, and pressure variations, in accordance with air flow into or out of the water column 84 in response to variation in water level. Detection of air flow through one or more apertures of the water column 84 enables sufficient working range, while enabling reduced height of the water column 84.

Figure 4:
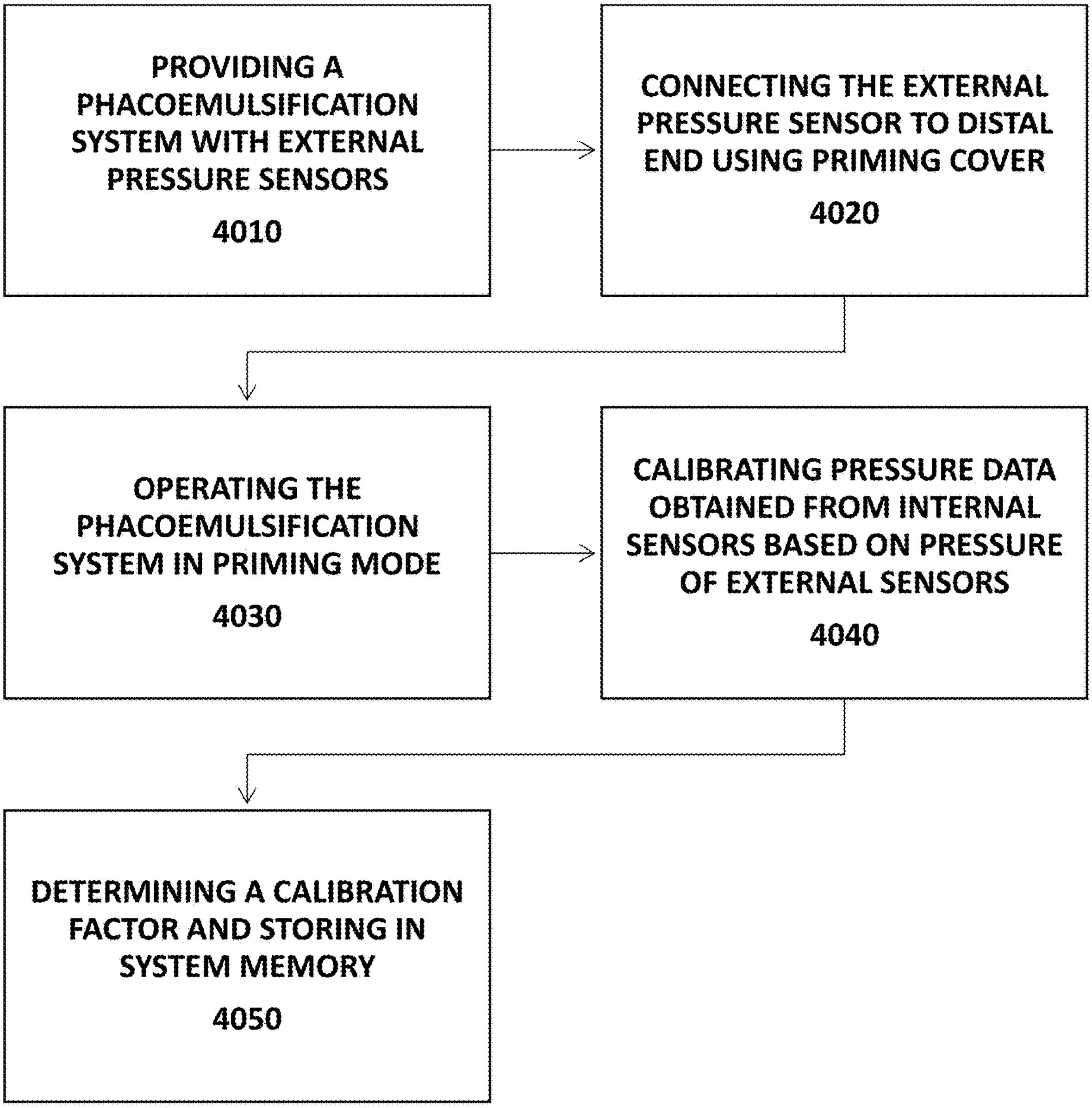
FIG. 4 exemplifies a method for use in priming of a phacoemulsification system according to some examples of the present disclosure.

Further, reference is made to FIG. 4, exemplifying a method for priming a phacoemulsification system. As shown, the method includes providing a phacoemulsification system and one or more external pressure sensors at step 4010. Connecting the external pressure sensors with the distal end of a handpiece of the system, via a priming cover, at step 4020. When the external sensor is coupled with the distal end via the priming cover, the method proceeds to operating the phacoemulsification system in a priming and/or tuning mode at step 4030. Operation in priming and/or tuning mode is used prior to operation of the system for a medical procedure, to fill irrigation and/or aspiration channels with fluid (e.g., balanced salt solution), remove air bubbles from the channels, and verify proper operation of the system. Additionally, according to some examples of the present disclosure, the method includes calibrating pressure data obtained from one or more sensors of the system based on calibration pressure data from the one or more external sensors 4040, determining a calibration factor and storing the calibration factor in a memory for use during system operation at step 4050.

This method provides for calibrating one or more sensors of the phacoemulsification system using pressure data collected by the one or more sensors of the system and the one or more external sensors. As indicated above, pressure data collected by one or more sensors of the system (e.g., sensors 116 in FIGS. 1 and 2) may vary from the pressure at distal end of the handpiece as a result from pressure and flow variation between the distal end of the handpiece and the sensors. This may be associated with irrigation and/or aspiration channels within the handpiece and/or the connection line (104 in FIGS. 1 and 2). Calibration of the one or more sensors is directed to align pressure data obtained by the one or more sensors of the system during operation of the system with actual pressure at the distal end of the handpiece. As indicated above, during priming of the phacoemulsification system, the technique of the present disclosure utilizes pressure data collected by the one or more sensors of the system, together with pressure data of the one or more external sensors, to calibrate the one or more sensors of the system. In some examples, the technique may also utilize additional parameters such as irrigation flow rate during priming, to enhance calibration. The calibration process may be used to determine a relation, or calibration factor, that is stored in a memory unit of the system. Further, during operation, the one or more processors of the phacoemulsification system may use the stored calibration factor to convert pressure data collected by the system's sensors and determine actual pressure conditions at the distal end of the handpiece.

As indicated above, in some examples, the actions 4010 and 4020 may include connecting a phacoemulsification system with a kit including priming cover as described in FIG. 3A or 3B above and using one or more external sensors for calibrating the system sensors with the pressure data as described herein.

Figure 5:
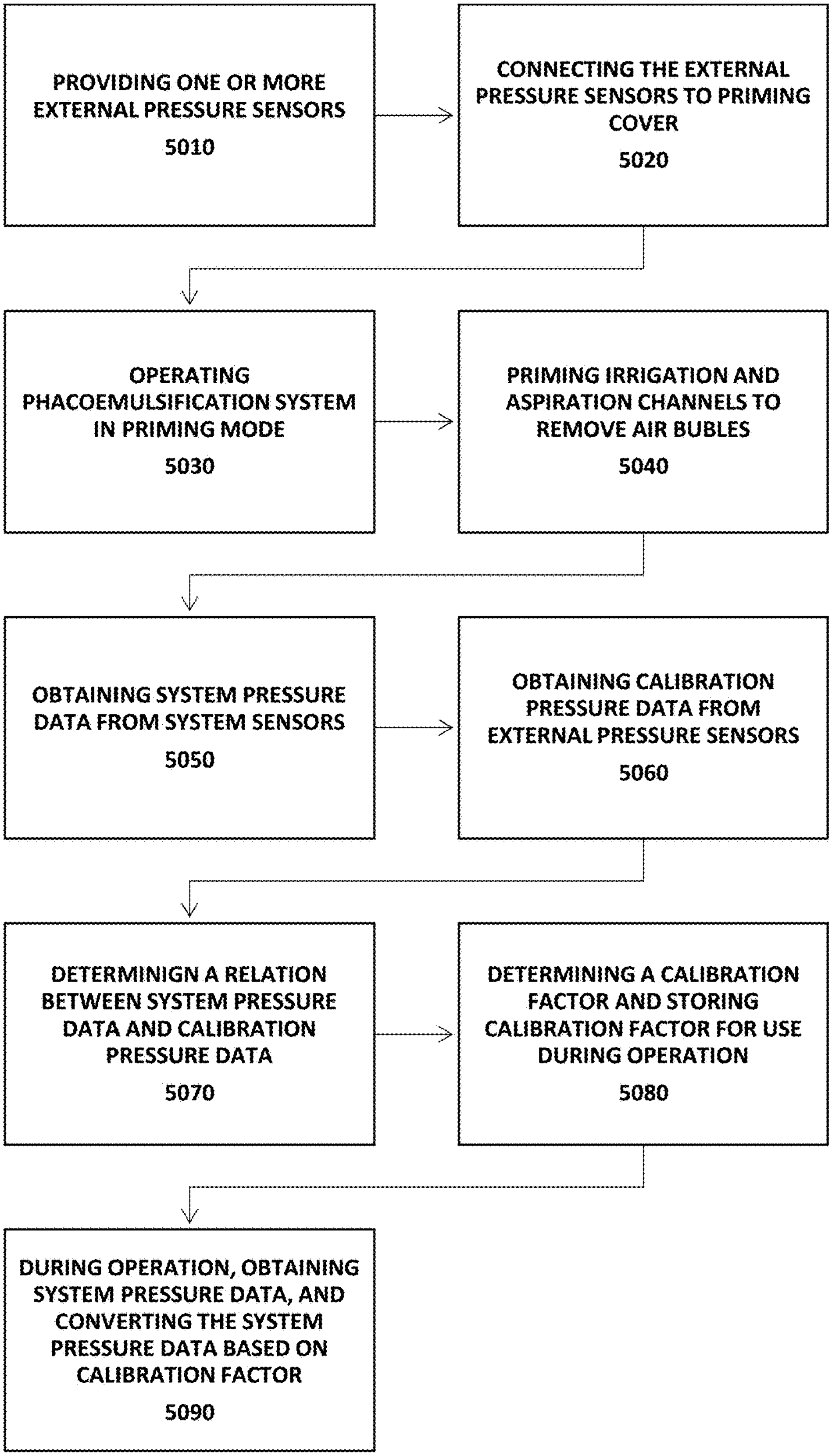
FIG. 5 exemplifies an additional method for use in priming of a phacoemulsification system according to some examples of the present disclosure.

FIG. 5 shows a further method for use in priming of a phacoemulsification system according to some examples of the present disclosure. In this example, the method includes providing one or more external pressure sensors in step 5010 and coupling the external pressure sensors with a priming cover and placing the priming cover over at least a portion of the distal end of the handpiece in step 5020. Operating a phacoemulsification system in a priming mode in step 5030. In the priming mode, the air (bubbles) in the irrigation and aspiration channels is removed in step 5040. Additionally, during the priming mode, the method includes operating the system (irrigation and aspiration modules) to obtain pressure data from the one or more system sensors at step 5050 and to obtain calibration pressure data from the external pressure sensors at step 5060. The system may operate the irrigation module for providing irrigation fluid in one or more different selected flow rates. And to operate the aspiration module for generating selected vacuum conditions, to provide variations in pressure conditions. Further, the method may include determining a relation between system pressure, collected by system sensors (e.g., 116 in FIGS. 1 and 2) and calibration pressure collected by external sensors 5070. As indicated above, such relation may be in the form of a function describing variation between the different pressure measurements. In some examples, the relation may be in the form of a lookup table specifying the calibration pressure measured for different operation conditions such as different flow rates and aspiration levels, and the pressure measured by the system sensors in the same operating conditions. Using the determined relation, the method may operate to determine a calibration factor and store the calibration factor for later use, e.g., in a memory unit at step at step 5080. The calibration factor may be a one- two- or multi-dimensional factor describing adjustment to pressure data collected by the system sensors to what would be the pressure if measured at the distal end of the handpiece. In some examples, the calibration factor may depend on system pressure data. In some examples, the calibration factor may depend on one or more additional operational characteristics such as irrigation rate, aspiration level, etc.

After priming, the phacoemulsification system may be ready for use in a medical procedure. During the medical procedure, the method may include obtaining pressure data from the system sensors and converting the pressure data in accordance with the stored calibration factor at step 5090. This provides output pressure data calibrated to pressure that would be measured at the distal end of the handpiece, where the system interfaces with a patient's eye. Accordingly, the method of the present disclosure may be used to enhance accuracy and reproducibility of pressure data during a medical operation using a phacoemulsification system, to eliminate, or at least significantly reduce complications during the medical procedure.

The present disclosure thus provides for a phacoemulsification system and a method for use in priming of a phacoemulsification system. The present technique utilizes one or more external sensors, in the meaning of measuring pressure at the distal end of the handpiece via a priming cover, for calibrating the system sensors using the pressure data collected.

EXAMPLES

Example 1: A phacoemulsification system (100) comprising:

- a handpiece (50) comprising a piezoelectric element (52) and a distal end comprising a needle (54) and a sleeve (55), wherein the distal end is configured to be inserted into an eye and to be vibrated by the piezoelectric element (52) to emulsify a lens of the eye;
- an irrigation module (112) configured to supply a flow of irrigation fluid into the eye, the irrigation module (112) comprises an irrigation channel having an outlet positioned at the distal end of the handpiece (50) so as to enable flow of irrigation fluid therethrough;
- an aspiration module (114) configured for aspiring eye fluid, the aspiration module (114) comprises an aspiration channel having an aspiration port positioned at the distal end of the handpiece (50) so as to enable flow of an eye fluid therethrough;
- a priming cover (56) configured to fit over the distal end of the handpiece (50) during a priming process;

one or more external pressure sensors (80) configured to be coupled with the priming cover (56);

one or more sensors (116) coupled with the irrigation channel or the aspiration channel and configured to monitor at least one of an irrigation pressure in the irrigation channel and an aspiration pressure in the aspiration channel; and one or more processors (118) configured, for upon actuation, operating a priming process including:

operating the irrigation module (112) to fill the irrigation channel with irrigation fluid so that the irrigation channel is free from air and irrigation fluid fills the priming cover;

wherein the one or more processors (118) being further configured for obtaining calibration pressure data from the one or more external pressure (80) sensors and for calibrating pressure output data of the one or more sensors (116) coupled with the irrigation channel or the aspiration channel based on the calibration pressure data.

Example 2: The phacoemulsification system of example 1, wherein the phacoemulsification system (100) further comprises a water column (84), wherein the one or more external pressure sensors (80) are coupled with the water column (84).

Example 3: The phacoemulsification system of example 2, wherein the water column (84) comprises one or more apertures (86) at atop surface thereof, and comprising one or more flow meters (88) configured for determining pressure variations in accordance with air flow through the one or more apertures.

Example 4: The phacoemulsification system (100) of any one of example 1 to 3, wherein the one or more external pressure sensors (80) comprises at least one capacitive pressure sensor.

Example 5: The phacoemulsification system (100) of any one of examples 1 to 4, wherein the one or more external pressure sensors (80) being fluidly coupled with the priming cover (56) and wherein the one or more external pressure sensors (80) are configured to determine fluid pressure at the operating handpiece (50) of the phacoemulsification system (100) during the priming process.

Example 6: The phacoemulsification system (100) of any one of examples 1 to 5, wherein the one or more processors (118) is adapted for determining a calibration factor defining a relation between the calibration pressure data obtained from the one or more external pressure sensors (80) and pressure data of the one or more sensors (116).

Example 7: The phacoemulsification system (100) of example 6, wherein said one or more processors (118) is configured to utilize said calibration factor for adjusting output data indicative of fluid pressure of said phacoemulsification system (100) during operation.

Example 8: A method for use in priming a phacoemulsification system, the method comprising:

providing at least one external pressure sensor (5010) to be coupled with a working end of a handpiece (50) of said phacoemulsification system (5020);

operating said phacoemulsification system for priming (5030) thereof while calibrating (5060) pressure data of one or more sensors (116) of said phacoemulsification system in accordance with pressure data of said at least one external pressure sensor (80).

Example 9: The method of example 8, further providing a water column (84) to be coupled with the working end of the handpiece (50) and said at least one pressure sensor (80).

Example 10: The method of example 8 or 9, wherein said at least one pressure sensor (80) comprises at least one capacitive sensor.

Example 11: The method of any one of examples 8 to 10, wherein said providing at least one external pressure sensor (80) coupled with a working end of said handpiece (50) comprises coupling said at least one pressure sensor with a priming cover (5020) configured for covering said working end of said handpiece (50), thereby providing said at least one external pressure sensor (80) to determine fluid pressure at said working end of said handpiece (50).

Example 12: The method of any one of examples 8 to 11, wherein said calibrating (5060) comprises determining a relation (5070) between output data indicative of fluid pressure of said phacoemulsification system (100) and pressure data of said at least one pressure sensor (80).

Example 13: The method of example 12, further comprising utilizing said relation between output data indicative of fluid pressure of said phacoemulsification system and pressure data of said at least one pressure sensor and determining a calibration factor (5080).

Example 14: The method of example 13, further comprising using said calibration factor for adjusting output data indicative of fluid pressure of said phacoemulsification system during operations (5090).

Example 15: A software program product, embedded in a non-transitory computer readable medium, comprising computer readable instructions that when executed by one or more processors (118) cause the processor to operate a phacoemulsification system (100) in a priming mode, comprising: receiving input handpiece pressure data from at least one external pressure sensor (80), and system pressure data from one or more sensors (116) of said phacoemulsification system (100), processing the handpiece pressure data and the system pressure data and determining a calibration factor (5080) defining a relation between the handpiece pressure data and the system pressure data, and calibrating the one or more sensors (116) of said phacoemulsification system in accordance with the calibration factor.

Example 16: The software product of example 15, comprising computer readable instructions for determining a calibration factor (5080) indicative of a relation between pressure data of said phacoemulsification system and pressure data of said at least one external pressure sensor, and to store said calibration factor is a storage utility.

Example 17: The software product of example 16, further comprising computer readable instructions for adjusting (5090) pressure output data of said phacoemulsification system in accordance with said calibration factor stored in a storage utility during operation.

It is to be noted that the various features described in the various examples can be combined according to all possible technical combinations.

It is to be understood that the invention is not limited in its application to the details set forth in the description contained herein or illustrated in the drawings. The invention is capable of other examples and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and systems for carrying out the several purposes of the presently disclosed subject matter.

Those skilled in the art will readily appreciate that various modifications and changes can be applied to the examples of the invention as hereinbefore described without departing from its scope, defined in and by the appended claims.

The invention claimed is:

1. A phacoemulsification system comprising:

a handpiece comprising a piezoelectric element and a distal end comprising a needle and a sleeve, wherein the distal end is configured to be inserted into an eye and to be vibrated by the piezoelectric element to emulsify a lens of the eye;

an irrigation module configured to supply a flow of irrigation fluid into the eye, the irrigation module comprises an irrigation channel having an outlet positioned at the distal end of the handpiece so as to enable flow of irrigation fluid therethrough;

an aspiration module configured for aspiring eye fluid, the aspiration module comprises an aspiration channel having an aspiration port positioned at the distal end of the handpiece so as to enable flow of an eye fluid therethrough;

a priming cover configured to fit over the distal end of the handpiece during a priming process;

one or more external pressure sensors configured to be coupled with the priming cover;

one or more sensors coupled with the irrigation channel or the aspiration channel and configured to monitor at least one of an irrigation pressure in the irrigation channel and an aspiration pressure in the aspiration channel; and one or more processors configured for, upon actuation, operating the priming process including:

operating the irrigation module to fill the irrigation channel with the irrigation fluid so that the irrigation channel is free from air and the irrigation fluid fills the priming cover;

wherein the one or more processors being further configured for obtaining calibration pressure data from the one or more external pressure sensors and for calibrating pressure output data of the one or more sensors coupled with the irrigation channel or the aspiration channel based on the calibration pressure data.

2. The phacoemulsification system of claim 1, wherein the phacoemulsification system further comprises a water column, wherein the one or more external pressure sensors are coupled with the water column.

3. The phacoemulsification system of claim 2, wherein the water column comprises one or more apertures at a top surface thereof, and comprising one or more flow meters configured for determining pressure variations in accordance with air flow through the one or more apertures.

4. The phacoemulsification system of claim 1, wherein the one or more external pressure sensors comprises at least one capacitive pressure sensor.

5. The phacoemulsification system of claim 1, wherein the one or more external pressure sensors being fluidly coupled with the priming cover and wherein the one or more external pressure sensors are configured to determine fluid pressure at the handpiece of the phacoemulsification system during the priming process.

6. The phacoemulsification system of claim 1, wherein the one or more processors is adapted for determining a calibration factor defining a relation between the calibration pressure data obtained from the one or more external pressure sensors and pressure data of the one or more sensors.

7. The phacoemulsification system of claim 6, wherein said one or more processors is configured to utilize said calibration factor for adjusting output data indicative of fluid pressure of said phacoemulsification system during operation.

* * * * *